United States Patent [19]

Wahl et al.

[11] 4,290,424
[45] Sep. 22, 1981

[54] PLASTER CUTTING WIRE, PLASTER CAST OR DRESSING COMPRISING SUCH WIRE AND METHOD OF MANUFACTURING SUCH A PLASTER CAST OR DRESSING

[75] Inventors: Karl I. Wahl, Ekerö; Lars G. Lindström, Sundbyberg, both of Sweden

[73] Assignee: Landstingens Inkopscentral, Ekonomisk Forening, Solna, Sweden

[21] Appl. No.: 96,296

[22] Filed: Nov. 21, 1979

[30] Foreign Application Priority Data

Nov. 29, 1978 [SE] Sweden .............................. 7812318

[51] Int. Cl.³ .............................................. A61F 5/04
[52] U.S. Cl. ................................................ 128/91 A
[58] Field of Search .................... 128/91 A, 91 R, 83, 128/87 R

[56] References Cited

U.S. PATENT DOCUMENTS 3,643,656 2/1972 Young et al. ..................... 128/91 A
3,867,931 2/1975 Babka ................................ 128/91 A

FOREIGN PATENT DOCUMENTS 888595 7/1953 Fed. Rep. of Germany ... 128/91 A
2148814 4/1973 Fed. Rep. of Germany ... 128/91 A
975024 10/1950 France ............................... 128/91 A Primary Examiner—John D. Yasko
Attorney, Agent, or Firm—Witherspoon & Hargest

[57] ABSTRACT

The present invention relates to a plaster cast cutting wire (1) permitting the simple removal of a plaster cast or dressing. The plaster cast cutting wire comprises an anchoring plate (2) from which two substantially equally long cutting wire ends (3) extend. The cutting wire is positioned against the limb or body portion to be dressed and the plaster-of-Paris bandage is wound around both the body portion and the plaster cutting wire, in a way causing the plate (2) to become embedded in the cast. In order to facilitate removal of the plaster cast or dressing at least two plaster cutting wires will normally be used, thereby providing for division of the plaster cast into at least two parts upon removal. If the plaster cast or dressing is to be applied over a joint, the plates (2) are positioned opposite the joint on the outer and inner sides thereof.

10 Claims, 5 Drawing Figures

PLASTER CUTTING WIRE, PLASTER CAST OR DRESSING COMPRISING SUCH WIRE AND METHOD OF MANUFACTURING SUCH A PLASTER CAST OR DRESSING

The present invention relates to plaster casts or dressings and in particular to a plaster cast cutting wire, a plaster cast containing such wire and a method of manufacturing such a plaster cast.

Removal of plaster casts or dressings from body portions has previously ordinarily been performed with the aid of tools, the plaster casts being cut open by means of a particular type of cutter of an oscillating saw blade. Normally, no other tools have been used.

There have been proposals in e.g. U.S. Pat. Nos. 2,523,837, 2,342,695 and 2,746,452 to incorporate wires or ribbons into plaster casts, such wires or ribbons subsequently being pulled with the aid of pulling tools through the plaster casts to be opened thereby. However, these known arrangements have been subjected to certain drawbacks preventing more general use thereof and restricting the use to occasional tests.

When a pulling wire or the like is inserted into a plaster cast for the purpose of subsequently opening the cast, two problems are encountered. One problem is to provide a pulling wire which is resistant to the pulling stresses encountered, and the second problem is presented by the necessity to have the pulling wire firmly anchored to enable it to perform its cutting action without getting detached. Under very ordinary circumstances the pulling wire is exposed to pulling stresses amounting to about 100–150 kp which means that the anchoring and positioning of the wire offer grave problems.

As far as the conventional methods of removing plaster casts are concerned, certain well-known problems are met. One factor is that the cost of the tools used is high both in acquisition and maintenance; a second factor is that these tools may create anxiety, in particular in children and elderly persons, a third factor being involved in the crushing of the plaster-of-Paris causing plaster dust to be formed with detrimental consequences in particular for persons professionally working with the opening of plaster casts or dressings.

In some cases it appears that a plaster cast has been removed too early, requiring a new plaster cast to be applied with consequential waste of material and time.

It is the purpose of the present invention to remove the above described disadvantages. This purpose is achieved by the means and method defined in the claims from which also the characteristic features of the invention appear.

The invention is described in detail by reference to the attached drawings in which.

Figure 4:
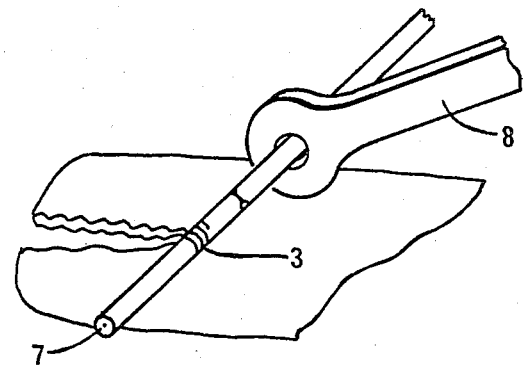
Figure 5:
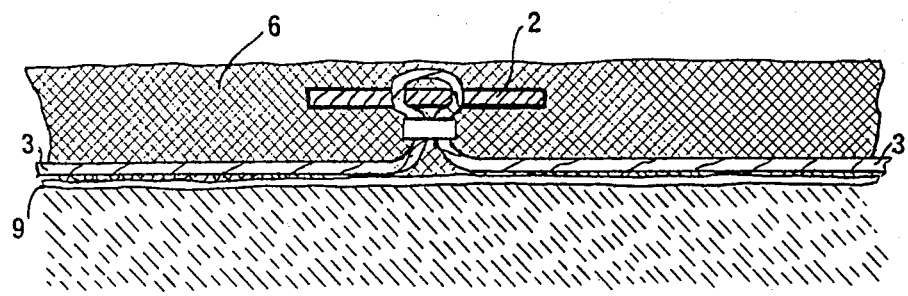

FIG. 4 schematically illustrates how the plaster cutting wire is pulled for opening the plaster cast; and FIG. 5 is a schematical fragmentary section of a plaster cast or dressing illustrating the anchoring of the cutting wire and its attachment plate in the plaster cast.

Figure 1:
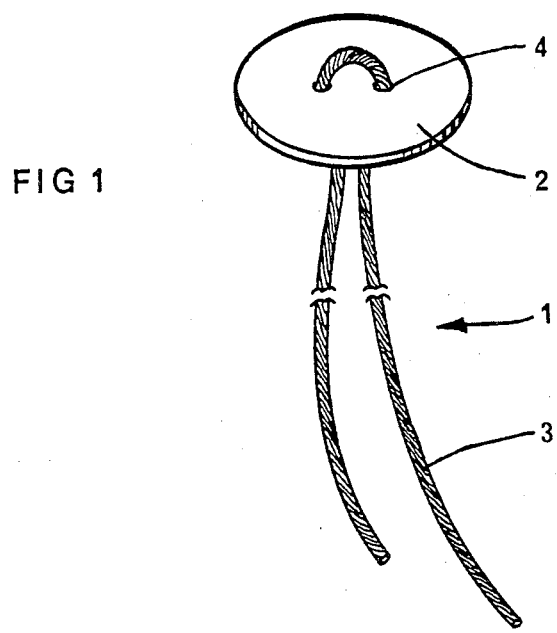
FIG. 1 is a perspective view of a plaster cutting wire according to the invention provided with an attachment plate.
Figure 2:
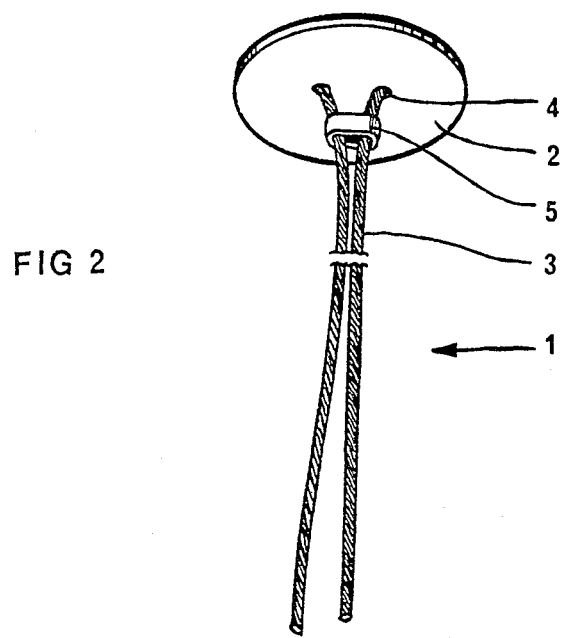
FIG. 2 is a perspective view of the plaster cutting wire according to FIG. 1 viewed against the opposite side of the attachment plate.

As initially mentioned, the anchoring of the plaster cutting wire is a factor of very great importance. The plaster cutting wire arrangement 1 shown in FIGS. 1 and 2 is provided with a plate 2 of non-corroding material to which the cutting wire 3 proper is attached. The cutting wire 3, in the embodiment shown, is passed through two holes 4 in plate 2, which thus resembles an ordinary button, the wire being latched by means of a clip 5 placed around the two extending portions of the cutting wire 3 adjacent plate. The two parts of cutting wire 3 are suitable equally long which means that plate 2 is positioned substantially in the middle of cutting wire 3.

Plate 2 may be designed in various ways. Thus, in order to avoid a time-consuming threading of the cutting wire 3 through holes in plate 2, the plate instead may be provided with two diametrically opposed slits having spaced inner ends to form a web portion. This web portion may have a width of about 10 mm sufficient to resist breakage of the plate under stress. Obviously the plate may have any shape such as circular or square without deviation from the basic inventive idea.

The cutting wire 3 may be resin-coated as a protection against corrosion and for the purpose of preventing the plaster-of-Paris to become attached thereto, which is an imminent risk when the cutting wire is a wire rope.

The resin coating is particularly useful in preventing a cutting wire rope from fraying-out when it is cut to suitable dimensions. Suitably, the cutting wire has such a length in its original state that it is sufficiently long for every place of use and, due to this, it may some time be necessary to reduce the length in order to avoid the difficulty of disposing the extending ends. To use wire rope as a cutting wire offers in turn the advantage that the wire easily may be positioned in any required curvature.

Figure 3:
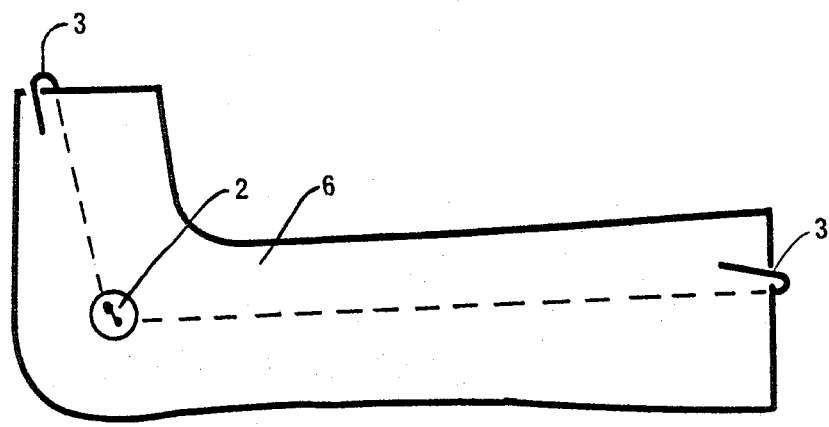
FIG. 3 is a schematical view showing how the plaster cutting wire is positioned in one type of a plaster cast or dressing.

FIG. 3 shows a surgical plaster dressing 6 adapted to extend over the ankle joint. As the dressing thus will be angular it is necessary to position plate 2 exactly in front of the joint on the outer and inner sides of the leg, as otherwise the cutting wire 3 might cut into the leg itself. From FIG. 4 in U.S. Pat. No. 2,342,695 it appears that this problem previously has not been appreciated because the wires are shown as extending on the forward and rear sides of the leg. When a pulling force is applied to the wire positioned below the heel, this wire will cut into the heel and when the opposite wire is pulled this will tend to crush or demolish the cast in front of the joint rather than cutting through the cast. These conditions in combination with the practically nonexistent attachments are responsible for the fact that the known device has not found acceptance for practical use because the essential problems have not been solved.

It is acknowledged in U.S. Pat. No. 2,523,837 that high pulling forces are encountered, the construction shown there accordingly comprising inter-position of a metal strip 10 between each layer of plaster in the cast. However, such a construction will be too expensive and too complicated both in manufacture and use to permit practical use of this construction.

In the present invention the attachment problem has been solved in a very simple way. No prior construction has ever considered positioning the attachment in the middle of the cutting wire rather than at one end thereof. By shaping and dimensioning the attachment plate as proposed in the present invention the problems encountered havebeen fully solved. As will appear from the following, the positioning of the plate itself is also a factor of importance.

In FIG. 4 there is schematically shown the opening of a plaster cast or dressing. One end of cutting wire 3 is attached to a cylindrical rod 7 to enable wire 3 to be wound-up by turning the rod 7. A handle 8 is provided to turn rod 7 by a reciprocating movement causing rod 7 to be turned in the one direction while releasing the rod in the opposite direction. Rod 7 continuously rides on the outer surface of the plaster casting which serves as a support during the pulling operation.

When in the normal case a plaster cast incorporates at least two plaster cutting wires, the cast, after having been opened, will consist of two or more parts. If, after X-ray examination, it appears that the cast has been removed too early, it is only necessary to reassemble the parts of the cast around the body portion or limb and to apply a new plaster bandage around. Obviously, also in this case plaster cutting wires are inserted in proper position to again yield a plaster cast equivalent to a new one but obtainable at a very low cost as far as material and work is concerned.

FIG. 5 illustrates the incorporation of plate 2 into the plaster cast. This is performed by adhesivably attaching the cutting wires to stocking 9 at some positions and subsequently winding the plaster bandages around the body portion to be dressed. Initially, the plaster bandages will be wound in below plate 2 to bring it to the position shown and only subsequently also over plate 2. When the cutting wire 3 is pulled for the purpose of opening plaster cast 6 plate 2 will offer a stable resistance thanks to the support given by the plaster cast. In spite of the large forces coming into action neither plate 2 nor cutting wire 3 can cause damage to the patient.

While the plaster cutting wire described in U.S. Pat. No. 2,342,695, as in the present invention, is positioned below the plaster cast to be pulled therethrough when the cast is removed, this known construction has not been developed to the extent necessary for practical use because the real problems have not been appreciated. In particular it has not been appreciated how a cutting wire of the type in question should be positioned in order not to inflict damage to an enclosed body portion, the known construction also being defective as far as the anchoring of the cutting wire is concerned. When pulling forces of a magnitude of 100–150 kp are encountered, not only a strong pulling wire but also a powerful anchoring are requested. Thanks to the present apparently simple but highly original invention it is now possible simply and quickly to open a plaster cast without using a tool frightening the patient and without any risk of injuring the patient.

What we claim is:

1. A cast cutting device comprising an anchoring plate including a plurality of apertures extending therethrough, a cutting wire extending through said apertures to support said plate, a first segment of said wire extending through a first of said apertures and a second segment of said wire extending through a second of said apertures, said plate being positioned upon said wire substantially intermediate the two ends thereof, and a latching means attached to said first and second segments of said wire for maintaining said plate in position relative to said wire.

2. Plaster cutting wire as claimed in claim 1, characterized in that a portion of the wire between its ends is attached to one side of the plate.

3. Plaster cutting wire as claimed in claim 2, characterized in that the wire in the shape of an eye extends through two holes or opposed slits in the plate.

4. Plaster cutting wire as claimed in any of preceding claims, characterized in that the cutting wire is resin-coated.

5. Plaster cast as claimed in claim 1, characterized in that the wire extends adjacent the inner surface of the plaster cast and that the plate is positioned within the plaster cast and having its surface approximately in parallel to the surfaces of the plaster cast.

6. In a plaster cast positioned against a body portion and of the class wherein said cast is removed by causing a cutting wire to be subjected to pulling stresses to cut through said cast, the combination with said cast of a cutting wire positioned adjacent said body portion, a portion of said cast extending around said body portion and said cutting wire, and an anchoring plate attached to said cutting wire in a position substantially intermediate the two ends thereof, a portion of said cast extending between said body portion and said plate and a portion of said cast being adjacent the surface of said plate furthest from said body portion to embed said plate within said cast and to space said plate from said body portion so that said wire may be pulled through said cast without said plate or said wire injuring said body portion.

7. The method of producing a plaster cast, comprising the steps of
placing a cutting wire, having an anchoring plate attached thereto intermediate the two ends thereof, adjacent a body portion;
embedding said wire and said body portion with a first portion of material which forms said cast while preventing said plate from being covered with said material; and,
embedding said plate between said first portion of material and a second portion of material which forms said cast.

8. The method of claim 7 wherein said body portion comprises a joint and which includes the step of placing said plate adjacent said joint and in a plane substantially parallel to the plane in which said body portion normally moves about said joint.

9. The method of claim 8 which includes the step of so placing a first of said cutting wires and said anchoring plates in a first of said parallel planes on one side of said joint and a second of said cutting wires and said anchoring plates in a second of said parallel planes on the opposing side of said joint.

10. The method of claim 7, which includes the step of positioning said plate such that its surfaces are substantially parallel to the surface of said cast when said plate is embedded in said material.

* * * * *